US008545425B2

(12) United States Patent
Lundtveit et al.

(10) Patent No.: US 8,545,425 B2
(45) Date of Patent: Oct. 1, 2013

(54) REUSABLE EFFLUENT DRAIN CONTAINER FOR DIALYSIS AND OTHER MEDICAL FLUID THERAPIES

(75) Inventors: Loren Lundtveit, Wadsworth, IL (US); Melissa Schubert, West Allis, WI (US); James Pappis, Clearwater, FL (US); Don A. Smith, Salem, WI (US)

(73) Assignees: Baxter International, Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 676 days.

(21) Appl. No.: 12/016,769

(22) Filed: Jan. 18, 2008

(65) Prior Publication Data
US 2009/0187138 A1 Jul. 23, 2009

(51) Int. Cl.
*A61M 37/00* (2006.01)
(52) U.S. Cl.
USPC .......................................... 604/4.01; 604/327
(58) Field of Classification Search
USPC ............... 604/29, 327, 4.01, 6.11, 6.15, 6.16, 604/19, 27, 317, 319, 322, 329, 540; 240/140
See application file for complete search history.

(56) References Cited

U.S. PATENT DOCUMENTS

| | | | |
|---|---|---|---|
| 2,083,479 A | 6/1937 | Speare | |
| 3,709,222 A * | 1/1973 | DeVries | 604/28 |
| 4,101,279 A | 7/1978 | Aslam | |
| 4,295,619 A | 10/1981 | Kulin et al. | |
| 4,387,873 A | 6/1983 | Pavlo et al. | |
| 4,527,716 A | 7/1985 | Haas et al. | |
| 4,560,472 A * | 12/1985 | Granzow et al. | 210/140 |
| 4,676,775 A | 6/1987 | Zolnierczyk et al. | |
| 4,902,282 A | 2/1990 | Bellotti et al. | |
| 5,001,788 A | 3/1991 | Pacelli | |
| 5,043,074 A | 8/1991 | Chevallet | |
| 5,053,003 A | 10/1991 | Dadson et al. | |
| 5,221,267 A | 6/1993 | Folden | |
| 5,349,995 A | 9/1994 | Perez | |
| 5,405,053 A | 4/1995 | Zublin | |
| 5,503,633 A | 4/1996 | Saunders et al. | |
| 5,671,485 A | 9/1997 | Middlestead | |
| 5,865,793 A | 2/1999 | Lo et al. | |

(Continued)

FOREIGN PATENT DOCUMENTS

DE 31 21 098 3/1982
EP 0 865 794 9/1998

(Continued)

OTHER PUBLICATIONS

International Search Report and Written Opinion for International Application No. PCT/US2009/030795 mailed on Jul. 6, 2009.

*Primary Examiner* — Jacqueline Stephens
*Assistant Examiner* — Benedict L Hanrahan
(74) *Attorney, Agent, or Firm* — K&L Gates LLP

(57) ABSTRACT

A dialysis system includes a source of dialysis fluid; at least one pump for pumping dialysate to or from a patient or dialyzer; and a drain container configured to receive effluent dialysis fluid from the patient or dialyzer through a drain tube, the drain container including an at least semi-rigid body, the body including a handle, a drain tube receiving portion, a spout, and wherein at least a portion of the body is non-opaque such that effluent dialysis fluid inside the at least semi-rigid body can be viewed.

14 Claims, 7 Drawing Sheets

(56) References Cited

U.S. PATENT DOCUMENTS

| | | |
|---|---|---|
| 5,876,396 A | 3/1999 | Lo et al. |
| 6,237,654 B1 | 5/2001 | Sheyer |
| 6,558,340 B1 * | 5/2003 | Traeger .................. 604/5.01 |
| 6,830,367 B2 | 12/2004 | Peterson et al. |
| 6,926,239 B1 | 8/2005 | DiMaggio |
| 6,953,069 B2 | 10/2005 | Galomb |
| 7,090,179 B2 | 8/2006 | DiMaggio |
| 7,090,180 B2 | 8/2006 | DiMaggio |
| 7,300,575 B2 | 11/2007 | Larson |
| 2003/0209884 A1 | 11/2003 | Joie et al. |
| 2005/0142312 A1 * | 6/2005 | Giblin et al. .................. 428/35.7 |

FOREIGN PATENT DOCUMENTS

| | | |
|---|---|---|
| EP | 1 398 018 | 3/2004 |
| WO | WO 9624396 | 8/1996 |
| WO | WO 2006052587 | 5/2006 |

* cited by examiner

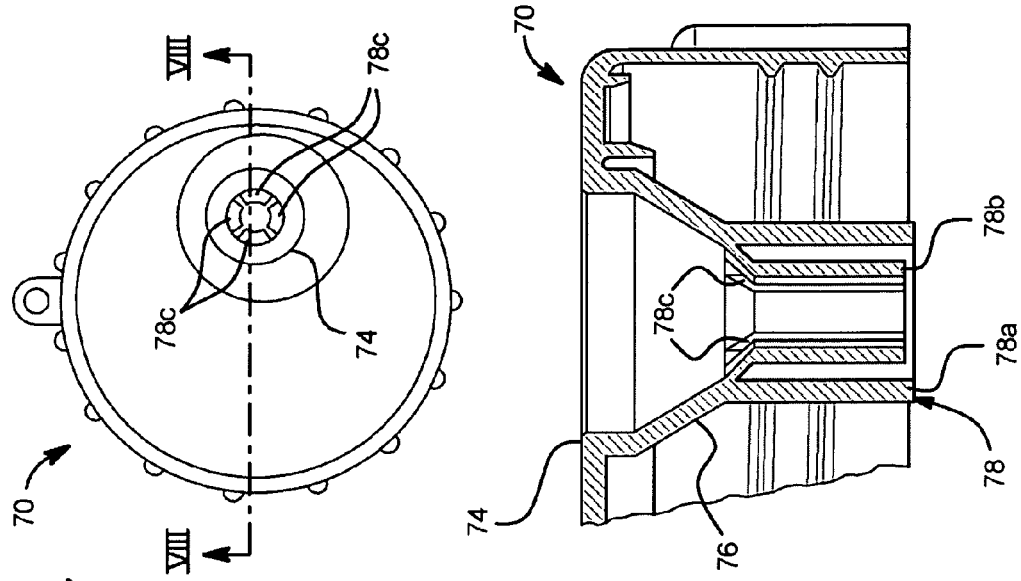
FIG. 7
FIG. 9
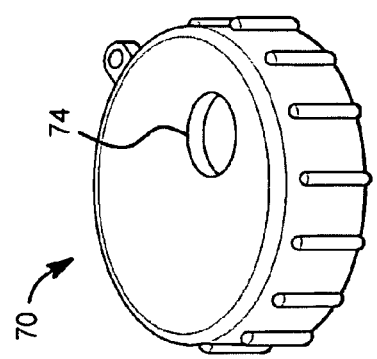
FIG. 6
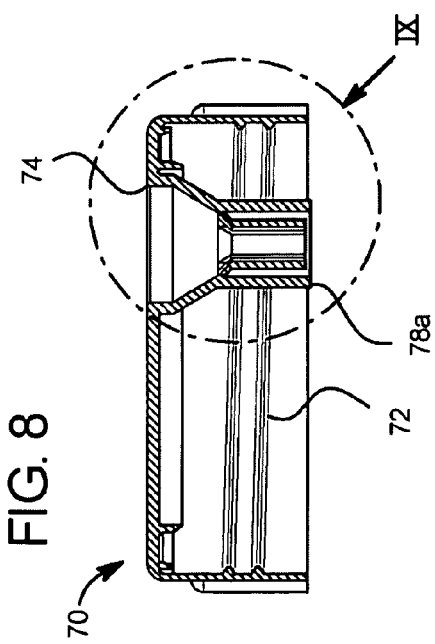
FIG. 8

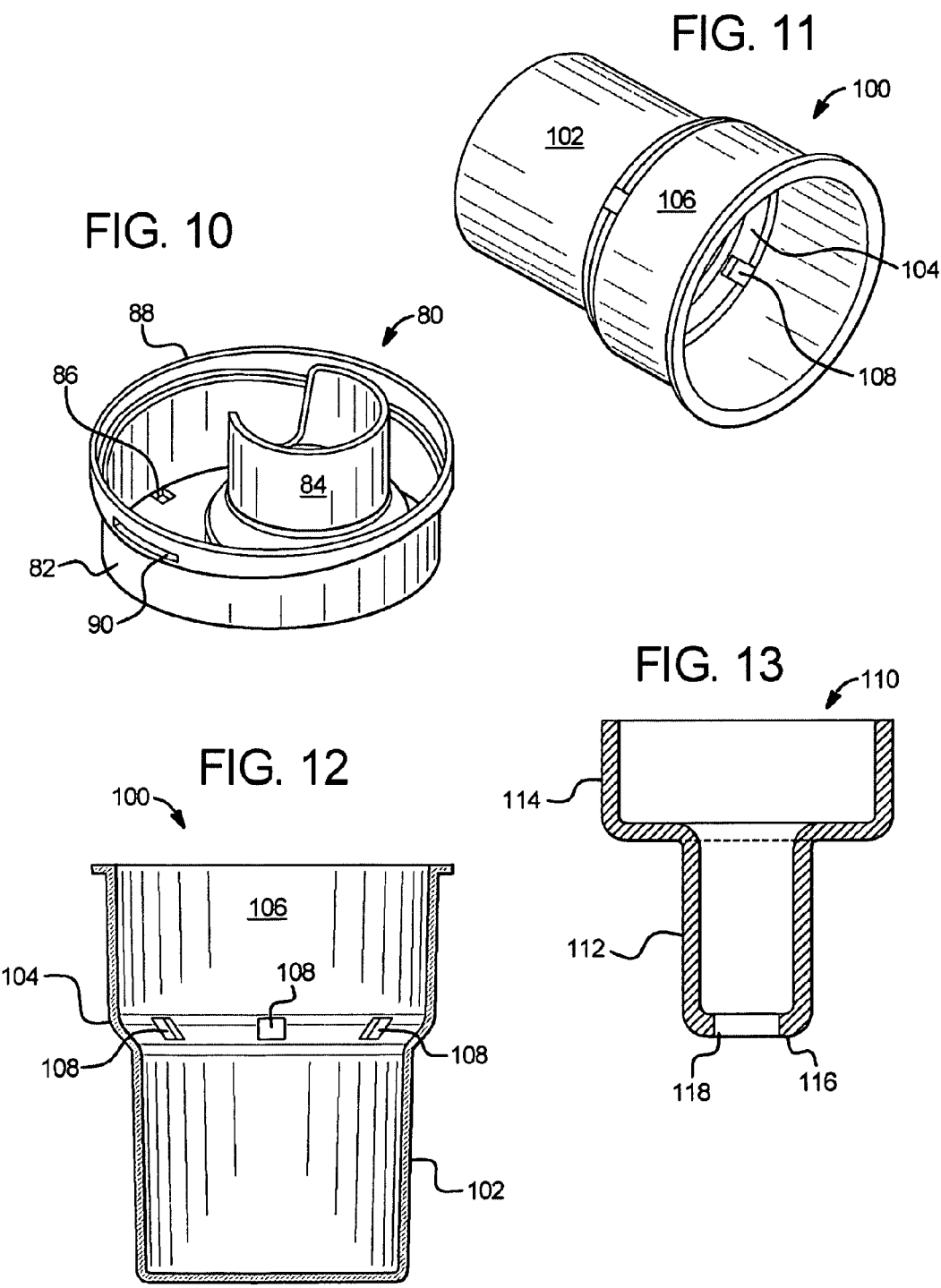

REUSABLE EFFLUENT DRAIN CONTAINER FOR DIALYSIS AND OTHER MEDICAL FLUID THERAPIES

BACKGROUND

The examples discussed below relate generally to medical fluid delivery. More particularly, the examples disclose systems, methods and apparatuses for dialysis such as hemodialysis ("HD") automated peritoneal dialysis ("APD").

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow for the dialysate to dwell within the cavity and for the transfer of waste, toxins and excess water to take place. The source can be multiple sterile dialysate solution bags.

APD machines pump spent dialysate from the peritoneal cavity, to the drain. As with the manual process, several drain, fill and dwell cycles occur during dialysis. A "last fill" occurs at the end of APD, which remains in the peritoneal cavity of the patient until the next treatment.

Regardless of the type of dialysis performed, the dialysis treatment will produce waste or effluent dialysis fluid, which is also referred to as drain fluid or "spent" dialysate. Spent dialysate can be sent to various places within the patient's home, such as the patient's bathtub or toilet. Alternatively, the effluent dialysate is sent to a drain bag. Both alternatives have disadvantages. Delivering spent dialysate to the patient's bathtub or toilet can require that long runs of tubing, which adds cost and can be a nuisance especially if the room in which therapy is performed is not close to a house drain. The drain areas of the house can also carry a large bioburden, which can be detrimental to a patient who is about to perform a sterile dialysis therapy. Drain bags collecting an entire treatment's worth of spent fluid can become heavy and difficult to move, especially for elderly patients. Drain bags are also disposable, adding to per therapy cost. The embodiments discussed herein attempt to address these disadvantages.

SUMMARY

The present disclosure provides a reusable drain container, which is easy to connect to, move and remove fluid from a medical fluid therapy system, such as a dialysis system. The container is rigid or semi-rigid, which aids in its transport. The container is sized to hold an entire therapy's worth of spent or effluent fluid. The container in one embodiment includes a front side and a back side opposite the front side. The container includes a top surface and a bottom surface. The container also includes two sides, forming a generally rectangular enclosure, although it is contemplated to make one or more of the sides more or less rounded. The container in various embodiments is made of plastic, composites, aluminum and combinations thereof.

The container is operable with any type of dialysis treatment that produces waster or effluent dialysate, such as any type of peritoneal dialysis treatment and any type of blood cleaning dialysis treatment. In the embodiments discussed below, the container is shown in connection with a peritoneal dialysis system, and in particular with an APD system using a weigh scale control of fluid fresh dialysate delivered to the patient and spent dialysate and ultrafiltrate ("UF") removed from the patient. It should be appreciated however that many of the teachings associated with the drain container are applicable to any type of dialysis treatment and to any type of dialysate and UF control.

With the weigh system, the container in one embodiment sits on a load cell during treatment such that the front of the container points upwardly and the back of the container rests on the load cell. A spent fluid inlet and spent fluid outlet are both provided on the front of the container, such that during treatment both the spent fluid inlet and spent fluid outlet point upwardly towards the dialysis instrument (which is located above the drain container in one implementation). The spent fluid inlet is therefore readily accessed. The spent fluid inlet and outlet are maintained elevationally above the drain fluid collected in the drain container during therapy, preventing leakage of the effluent fluid from the inlet or outlet.

In one embodiment, the back of the container, which rests on the load cell during treatment, includes a key feature, which mates with a key feature associated with the load cell. The mating key features prevent the patient from incorrectly loading the container onto the load cell, which can be important for proper operation of the load cell system. The mating key features also tend to hold the container in place when subjected to inadvertent bumping or forces. The mating key features further tend to prevent misuse with a generic container or bucket.

The container in one embodiment includes wheels for transporting the container from the dialysis instrument to a house drain, e.g., sink, toilet, shower, bathtub or floor drain. The load cell includes wheel tracks. When therapy is complete, the patient tilts the container such that the key feature of the container lifts free from the key feature of the load cell. The patient then rolls the container along the tracks off of the, e.g., slanted, load cell, onto the ground, and to the house drain.

When the container is lifted from the load cell, it is tilted such that the top of the container, which includes a handle, points upwardly and is accessible. The spent fluid outlet, located towards the bottom of the container on the front side of the container is positioned near the ground.

The wheels can be connected directly to the container or to an assembly to which the container is removeably attached. The wheel assembly can have a telescoping handle, which the patient can pull away from the container so that the patient does not have to bend over to pull the container to the house drain. The telescoping handle can be provided in addition to or in place of a handle formed integrally with the container.

The container also includes a number of helpful features for the removal of effluent from the container to drain once the patient has wheeled the container from the dialysis instrument to the house drain. For example, the container in one embodiment includes an indent or groove that holds the container in place on the rim of a toilet, bathtub, which allows for hands free removal of a cap from the spent fluid outlet. Also, the container includes a spout, which is exposed once the cap is removed. The spout directs effluent fluid from the container into the house drain in a smooth manner to reduce splashing and spilling. The spout is removable from the container in one implementation for cleaning purposes.

The container also includes features for viewing and sampling the effluent or spent dialysate. For example, the front or top of the container can have one or more window for viewing the drained liquid within the container. Alternatively, one or more of the spent fluid inlet or spent fluid outlet caps can be clear or transparent for viewing effluent within the container. Still further, the container can be sealed together from separate pieces, one or more of which is clear or transparent for viewing the color and consistency of the effluent fluid. In any case, viewing effluent is important because a certain color effluent can indicate that the patient is on the verge of suffering from peritonitis. To this end, it is contemplated to provide printed text and/or colored surfaces, which aid the patient in determining if the effluent is cloudy (onset of peritonitis).

The container in one embodiment also includes a sample reservoir, which automatically fills with fluid, and which can be removed from the container, so that the patient can take the sample to a dialysis center or other qualified facility for analysis. The reservoir in one embodiment traps the fluid sample and allows it to be removed from the container without having to pour out a sample.

It is also contemplated to size one of the inlet and outlet caps so as to hold an appropriate amount of a cleanser, e.g., bleach, which is used to clean and disinfect the container after a number of uses. For example, the spent fluid outlet cap can be sized for such use, while the spent fluid inlet cap is provided with a tubing port configured to accept and seal to a drain tube running from the dialysis instrument to the container.

It is therefore an advantage of the present disclosure to provide a reusable medical fluid drain container.

It is another advantage of the present disclosure to provide a drain container that is transported readily from the dialysis instrument to a house drain, reducing the amount of tubing needed to run directly from the instrument to the house drain.

It is a further advantage of the present disclosure to provide a draining system, which provides a ready apparatus for taking effluent samples.

It is yet another advantage of the present disclosure to provide a dialysis drain container, which provides a ready apparatus for viewing effluent dialysate to detect onset of peritonitis.

Additional features and advantages are described herein, and will be apparent from, the following Detailed Description and the figures.

BRIEF DESCRIPTION OF THE FIGURES

FIG. 6 is a perspective view of one embodiment of an inlet cap useable with the drain container of FIG. 1.

FIG. 7 is a top plan view of the inlet cap of FIG. 6.

FIG. 8 is a sectioned elevation view taken along line VIII-VIII of FIG. 7.

FIG. 9 is a sectioned elevation view taken at detail IX of FIG. 8.

FIG. 10 is a perspective view of one embodiment of a spout useable with the drain container of FIG. 1.

FIG. 11 is a perspective view of one embodiment of a sample reservoir useable with the drain container of FIG. 1.

FIG. 12 is a sectioned elevation view of the sample reservoir of FIG. 11.

FIG. 13 is a sectioned elevation view of one embodiment of a tube stop useable with the drain container of FIG. 1.

DETAILED DESCRIPTION

Figure 1:
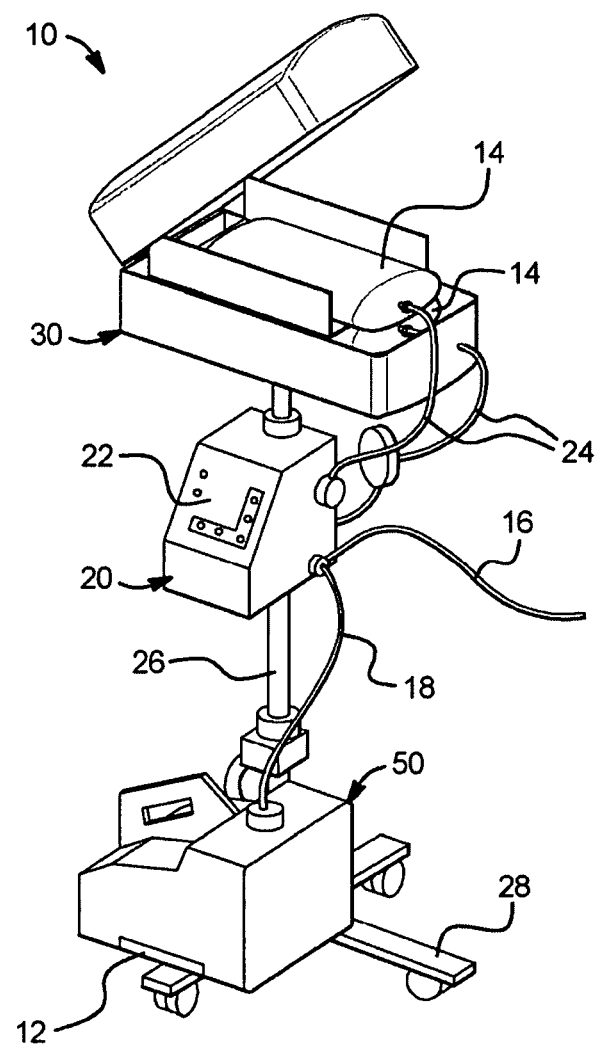
FIG. 1 is a perspective view of a medical fluid delivery system operating with one embodiment of the drain container of the present disclosure.

Referring now to the drawings and in particular to FIG. 1, system 10 illustrates a medical fluid system, such as a dialysis system, that can use the varies drain containers discussed herein. While the drain containers can be used with other types of medical fluid treatments, dialysis and in particular peritoneal dialysis provides one particularly well suited application. System 10 in the illustrated embodiment is an automated peritoneal dialysis ("APD") system. Various techniques have been developed to monitor the amount of dialysate delivered and removed from the patient as well as amount of the patient's body fluid or ultrafiltrate, which is also removed from the patient undergoing APD. In the illustrated embodiment, system 10 operates with a load cell 12. The load cell is discussed in more detail below in connection with FIG. 18. It should be appreciated however that the drain containers discussed herein can operate with APD systems having volumetric control systems other than load cells. Further, the drain containers discussed herein can operate with other types of peritoneal dialysis than APD, such as continuous ambulatory peritoneal dialysis ("CAPD"), which is generally considered to be a manual form of PD.

System 10 also includes an instrument 20, which includes a control panel 22 allowing the operator or patient to set begin and monitor treatment. Instrument 20 also includes valve and pump actuators that operate with disposable fluid tubes to distribute medical fluid, such as dialysate to a desired destination. Instrument 20 in one embodiment operates with pinch valves that pinch various parts of a tubing set to control the flow of fresh and spent dialysate to a desired destination. Alternatively, instrument 20 operates a disposable cassette, which can include cassette sheating that is selectively closed against or opened from rigid valve at various places to produce a desired valve state. Instrument 20 can include a plurality of pumps for pumping dialysis fluid to and from a patient or dialyzer.

In the illustrated embodiment, the instrument uses a pump or gravity to feed fresh fluid from a supply bag 14 to the patient through a patient line 16 and uses a pump or gravity to feed spent or effluent fluid from the patient to a drain container 50 via a pump (not illustrated) located within instrument 20 via a drain line 18. Supply bags 14 are located on a heater 30, which can be a resistive heater. Heater 30 heats dialysate to a desirable temperature for treatment, such as 37° C. Fluid flows from supply bags 14 and heater 30 via a pump or gravity through a supply line 24 from each supply bag 14 to instrument 20. When certain one or more valve is open, the heated fluid from supply line 24 flows through the disposable including patient line 16 to the patient.

As discussed above, the amount of effluent fluid flowing from the patient to drain container 50 through drain line 18 is weighed at load cell 12. That weight can be compared against a known weight of supply bags 14 to determine an amount of ultrafiltrate ("UF") that has been removed from the patient. Alternatively, instrument 20 can include a weigh scale that weighs the amount of fresh fluid contained in supply bags 14. Here, a controller within instrument 20 subtracts the beginning weight of fluid in supply bags 14 from the weight of fluid collected in container 50 to determine the amount of UF removed from the patient.

System 10 also includes a stand 26, which is connected to a wheeled base 28, which allows system 10 to be moved within the patient's house or within a center or hospital. One system and method for operating system 10 is discussed in copending patent applications entitled: "Automated Dialysis System Driven By Gravity And Vacuum", filed May 26, 2006, Ser. No. 11/420,608, the entire contents of which are incorporated herein expressly by reference and relied upon.

Referring now to FIGS. 2 to 5, container 50a illustrates one embodiment of a drain container of the present disclosure. Container 50a includes a front side 52, rear side 54, top surface 56 and bottom surface 58. In FIG. 1, container 50 is shown such that its front surface 52 points upwardly towards dialysis instrument 20. This configuration is advantageous because the drain fluid inlet and drain fluid outlet are provided on front surface 52 and are accordingly pointed towards dialysis instrument 20 and located elevationally above the drain fluid as the fluid fills within container 50 during operation. As shown below, when it is time to roll drain container 50 to a place to remove fluid from the container, the container is tilted such that top surface 56 points upwardly, and so that the patient can grab a handle 60 located at top surface 56. In one embodiment, drain container 50a is plastic, such as polypropylene ("PP"), high density polyethylene ("HDPE"), low density Polyethylene ("LDPE"), polycarbonate ("PC"), glycol-modified polyethylene terephthalate ("PET-G"), polyvinyl chloride ("PVC"); a composite material; aluminum and combinations thereof. Drain container 50a in one embodiment has a wall thickness, which is generally uniform, and which can be from about 1 mm to about 7 mm, e.g., 4 mm. Container 50a defines an internal volume that is sized for the particular medical fluid application. For dialysis treatment, such as peritoneal dialysis treatment, container 50a is sized to hold an entire treatment's worth of drain fluid. Container 52a can therefore be configured to hold from about five to about forty liters, e.g., eighteen liters, of effluent fluid.

As discussed above, front surface 52 of container 50a includes or defines a spent fluid inlet 62 and a spent fluid outlet 64. Inlet 62 and outlet 64 in one embodiment are threaded ports that matingly receive threaded caps as discussed in detail below. Spent fluid outlet 64 is located near bottom surface 58, so that when the patient or caregiver pulls drain container 50a to a toilet, tub or house drain, outlet 64 will be located elevationally below handle 60, so that the patient or caregiver can readily drain effluent fluid from drain container 50a. Spent fluid inlet 62 is located closer to top 56 of container 50a, such that when the patient or caregiver tilts drain container 50a using handle 60, inlet 62 is likewise raised elevationally, allowing the patient to more readily remove drain line 18 from the inlet cap (shown below). The patient or caregiver can thereafter pull drain container 50a to a house drain.

Figure 2:
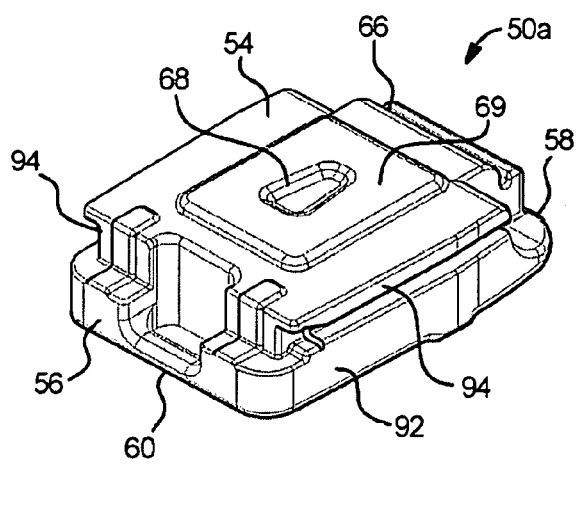
FIG. 2 is a perspective view of one embodiment of a drain container of the present disclosure.
Figure 3:
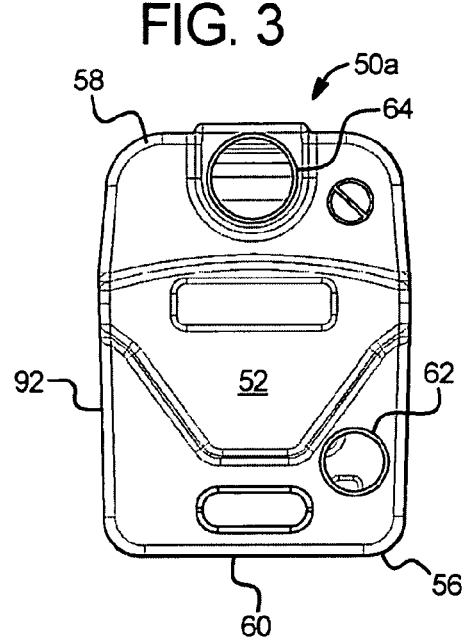
FIG. 3 is a front view of the drain container of FIG. 2.
Figure 5:
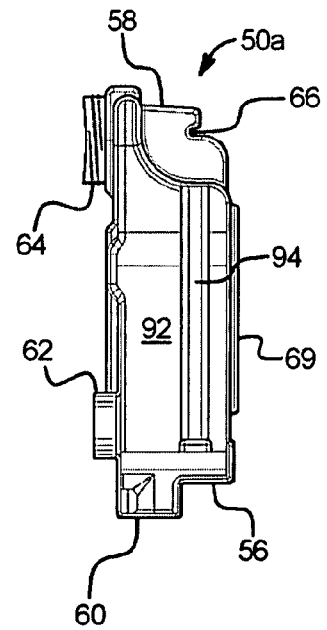
FIG. 5 is a side view of the drain container of FIG. 2.

As seen in FIGS. 2 and 5, bottom 58 of drain container 50a includes or defines a slot or groove 66, which is sized and shaped to snap-fit over an axle of a wheel assembly. One suitable wheel assembly is discussed below in connection with FIG. 17. FIGS. 2 and 5 also illustrate that side surfaces 92 of drain container 50a include or define grooves or slots 94 that mate with a frame of the wheeled assembly, such as the assembly shown below in connection with FIG. 17. In one embodiment drain container 50a is removable from the wheel assembly via snap-fitting slot or groove 66. Although not illustrated, bottom 58 of drain container 50a in one embodiment also includes apparatus configured to hold the drain container in place when the drain container is placed on a toilet or bathtub to drain from outlet 64 to the toilet or bathtub.

Figure 4:
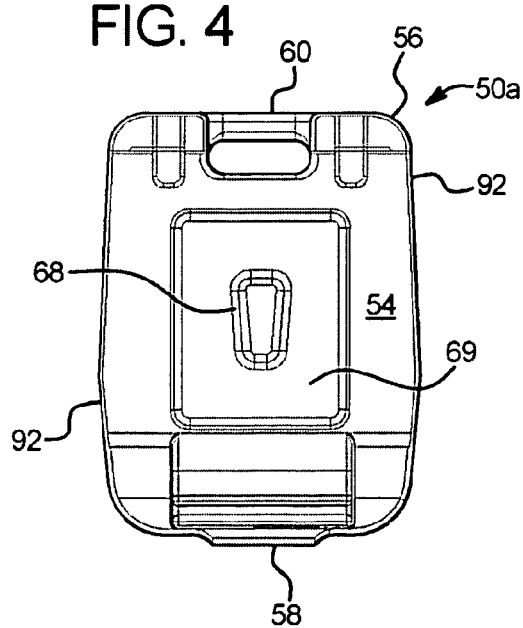
FIG. 4 is a rear view of the drain container of FIG. 2.

FIGS. 2 and 4 also show that rear surface 54 includes or defines an indented or female key structure 68. Indented key structure 50 is sized and configured to mate with a corresponding projecting or male key structure on the load cell when drain container 50a is placed in position for treatment. The keyed interfaced between drain container 50a and load cell is discussed in detail below in connection with FIG. 18.

Referring now to FIGS. 6 to 9, cap 70 illustrates one embodiment of a spent fluid inlet cap, which is suitable for use with container 50a of FIGS. 2 to 5. Inlet cap 70 can be made of certain of the materials specified above for drain container 50a, such as, PC, PET-G, PVC and polycarbonate polyester blend, which can each be clear for cap 70, which is clear in one embodiment. Cap 70 can have a nominal wall thickness of about 1 mm to about 7 mm, e.g., about 4 mm. Cap 70 in an embodiment is sized to thread onto spent fluid inlet 62 of drain container 50a, as seen best in FIGS. 3 and 5. While cap 70 is shown being configured to mate with inlet 62 via a threaded relationship, it should be appreciated that cap 70 could fit sealingly to inlet 62 via a snap-fitting and/or hinged manner.

FIG. 8 illustrates cap 70 having internal threads 72 that mate with external threads of inlet 62 of drain container 50a. Cap 70 further defines a drain tube opening 74. As seen most clearly in FIGS. 8 and 9, drain tube opening 74 tapers at flared annular wall 76 to form a drain tube 18 accepting area. Flared annular wall 76 extends inward to a port 78, which includes inner and outer cylindrical extensions 78a and 78b, respectively. Drain line 18 is inserted into the inlet cap 70 through splices 78c, through extension 78b and then into the tube stop 110 shown in FIG. 13, which is fitted to outer cylindrical extensions 78. The inner diameter (e.g., 18 mm-2*thickness of wall 114) of tube stop larger diameter portion 114 is solvent bonded or otherwise adhered to the outside of outer cylindrical extensions 78a (e.g., 15.6 mm OD). After passing through splices 78c and extension 78b, the tubing seals against the inner diameter of smaller diameter portion 112 of the tube stop 110 of FIG. 13 and bottoms out against cap 116 of tube stop 110.

Referring now to FIG. 10, spout 80 illustrates one suitable spout for operation with drain container 50a. Spout 80 can be made of any of the material specified above for drain container 80. Spout 80 can have a nominal wall thickness of about 2 mm to about 7 mm. In the present embodiment, spout 80 is configured to fit sealingly into outlet 64 of drain container 50a. Spout 80 includes a basin portion 82, which is sized to collect any effluent that may spill out of a funnel portion 84 during the effluent fluid removal process. Basin 82 also defines an opening 86, which allows air to enter drain container 50a while effluent fluid is poured smoothly out of funnel 84 of spout 80.

Basin 82 extends upward to a rim 88, which has a larger diameter than basin 82. Rim 88 is sized to press-fit to an inner wall of spent fluid outlet 64 of drain container 50a in such a manner that outwardly extending threads of spent fluid outlet 64 (in one embodiment) are left free to be threaded to an outlet cap, which is inserted over spout. Rim 80 includes or defines one or more locking aperture or projection 90, which locks to a mating projection or aperture, respectively, of the inlet wall of spent fluid outlet 64 when spout 80 is press-fit to drain container 50a. Projection or aperture 90 locks spout 80 in place with drain container 50a and prevents spout 80 from being pushed into the drain fluid collecting chamber of container 50a.

It should be appreciated that spout 80 can be formed integrally with container 50a in an alternative embodiment. For purposes of cleaning reusable drain container 50a, however, it may be desirable to provide spout 80 a separate piece, as illustrated, which can be cleaned separately, and which allows spent fluid outlet 64 to have a larger diameter, so that debris within container 50a can be readily flushed out from within the container.

Referring now to FIGS. 11 and 12, reservoir 100 illustrates one suitable reservoir for use with drain container 50a. Reservoir 100 allows the patient or caregiver to remove a sample of the drained or spent fluid, e.g., spent dialysate, in a clean and efficient manner. In certain medical therapies, such as dialysis, it is necessary that the patient or caregiver take a sample of the spent fluid from the patient to a hospital or laboratory for analysis. The spent fluid tells the hospital many important things, such as the effectiveness of the patient's treatment, the effectiveness in removing different or certain impurities contained within the effluent, and whether the patient is at risk for any of variety of infections, such as peritonitis common in dialysis.

Reservoir 100 can be made of any of the materials discussed above for container 50a. In an embodiment reservoir 100 has a nominal thickness of about 1 mm to about 7 mm, e.g., 4 mm. Reservoir 100 in one embodiment is made of a clear material, such as those above for inlet cap 70, so that the patient or caregiver can view the effluent fluid when reservoir 100 is removed from the drain container. It is known for dialysis that cloudy effluent can indicate the onset of peritonitis. Alternatively or additionally, it is contemplated to make part of drain container 50a clear or transparent, so that the patient can see the effluent within drain container 50a. For example, drain container 50a could be glued or welded together from two or more pieces, wherein one or more of the pieces (e.g., front surface 52) is clear or transparent. For alternatively or additionally, one of the inlet and outlet caps can be clear or transparent.

Reservoir 100 includes a fluid holding portion 102, a fluid entry portion 104 and container mating portion 106. Fluid holding portion 102 is sized to hold a sufficient sample volume for the patient to take to a hospital or clinic. Fluid entry portion 104 tapers outwardly from fluid holding portion 102. Fluid entry portion 104 defines a plurality of entry holes 108 that allow effluent fluid that enters drain container 50a to flow into and be held by fluid holding portion 102.

Portions 102, 104 and 106 are generally cylindrical as illustrated. Different cross-sectional shapes could be provided alternatively. Container mounting portion 106 is sized to fit sealingly on front surface 52 of container 50a, for example. Placing reservoir 100 on front surface 52 allows reservoir 100 to extend downwardly into the container and become filled when the effluent fluid rises close to front surface 52 (which is the upper surface during treatment) of drain container 50a. Accordingly, container mounting portion 106 is configured to extend a distance sufficient to set fluid holding portion 102 down into the container, so that the container does not have to be completely full for effluent fluid to begin to flow into apertures 108 of reservoir 100. Apertures 108 are overflow slots that allow effluent to spill into reservoir 100 throughout therapy.

Referring now to FIG. 13, tube stop 110 illustrates one suitable tube stop for container 50a. Tube stop 110 can be made of any of the materials discussed above for container 50a. Tube stop 110 can have a nominal thickness of about 1 mm to about 6 mm, e.g., 4 mm. Tube stop 110 includes a smaller diameter portion 112, which flanges out to a larger diameter portion 114. Smaller diameter portion 112 is capped at tube stop end 116. As discussed above, drain tube 18 seals to the inside of smaller diameter portion 112 and abuts tube stop end 116 when inserted into cap 70 and tube stop 110. Larger diameter portion 114 is solvent bonded or otherwise connected to outer projection 78a of cap 70. Tube stop 110 is illustrated as being generally cylindrical, however, the tube stop can have different cross-sectional shapes as desired.

Figure 14:
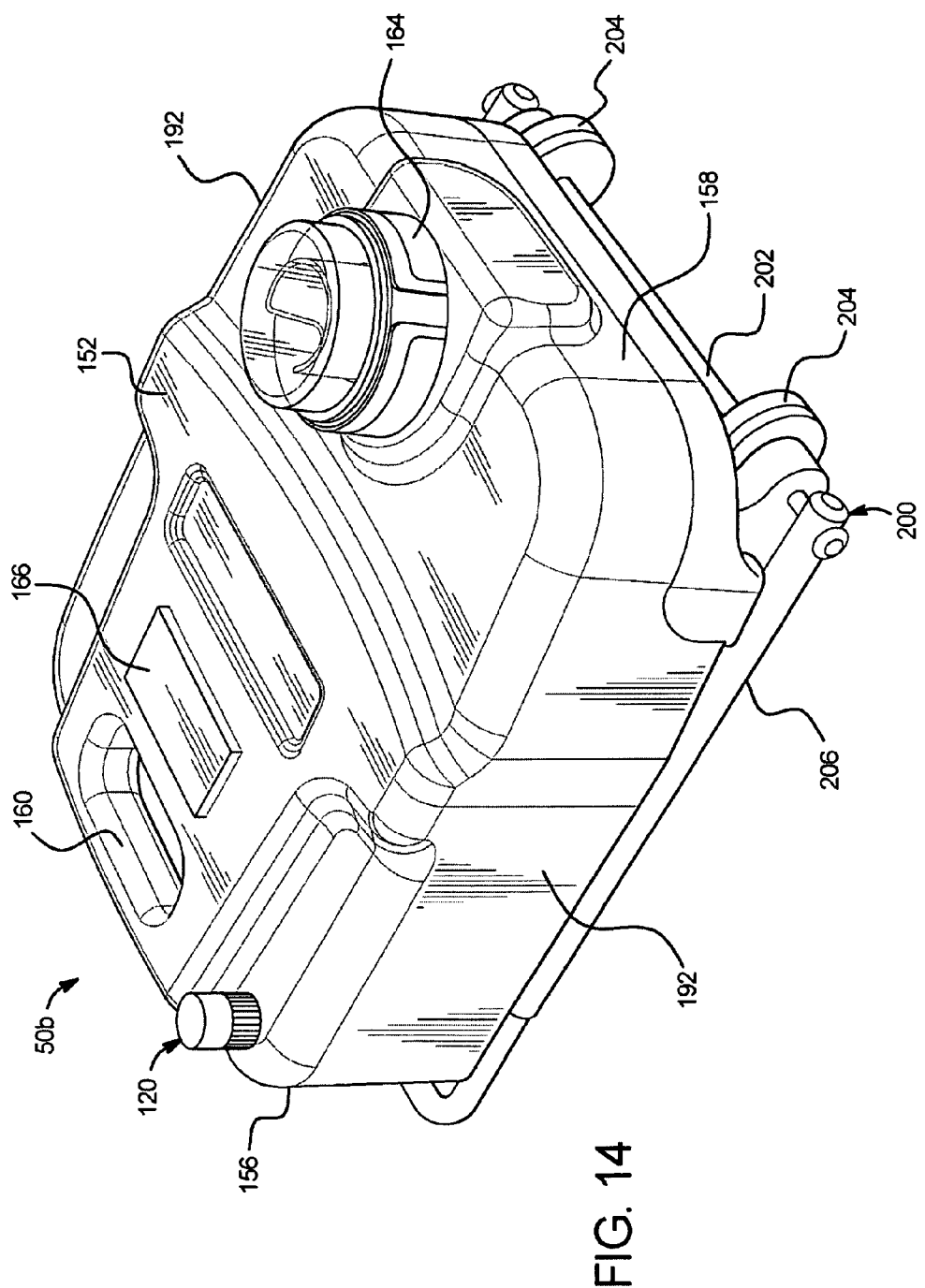
FIG. 14 is a perspective view of another embodiment of a drain container of the present disclosure.
Figure 15:
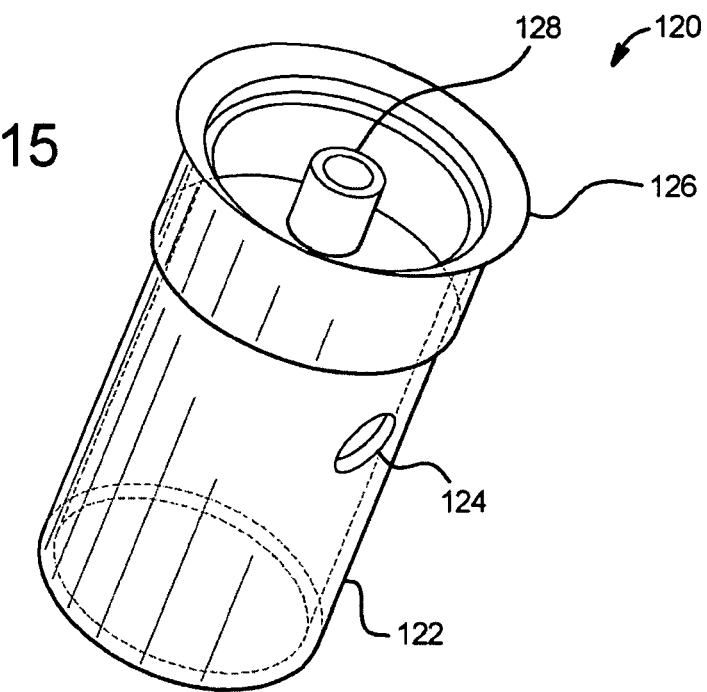
FIG. 15 is a perspective view of one embodiment of a sample reservoir useable with the drain container of FIG. 14.

Referring now to FIGS. 14 and 15, drain container 50b illustrates one alternative drain container of the present disclosure. Drain container 50b includes many of the same components as drain container 50a, such as a front surface 152, a rear surface (not seen in FIG. 14) a top surface 156, a bottom surface 158 and side surfaces 192. Top surface 156 includes a handle 160, which in both embodiments 50a and 50b is located closer to the front surface (52/152) of the respective container. Handles 60 and 160 are sized for one-handed operation in one embodiment.

Figure 17:
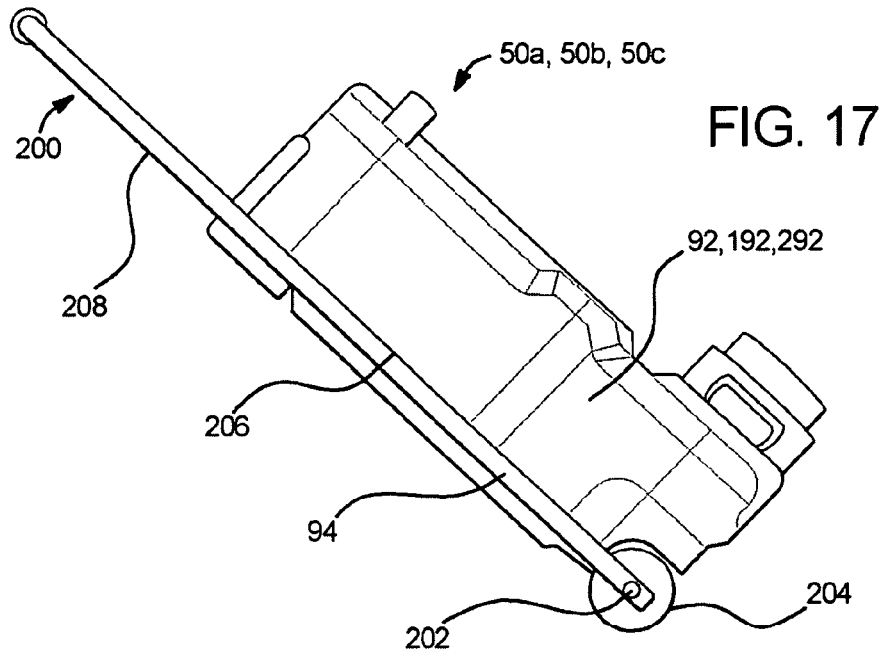
FIG. 17 is a side view of a telescoping wheel assembly useable with any of the drain containers discussed herein.

Bottom surface 158 of container 50b includes a snap-fitting groove (not seen), which snap-fits to an axial 202 of a wheel assembly 200 shown in FIG. 14 and in further detail in FIG. 17. As further seen in FIG. 14, assembly 200 includes frame members 206 that connect to axle 202 of wheel assembly 200 and slide into grooves at the sides of container, such as grooves 94 at sides 92 of container 50a. Although not seen in FIG. 14, sides 192 of container 50b include or define similar grooves or slots that are configured to accept members 206 of frame 200.

Drain container 50b also includes an effluent fluid outlet 164, which is shown capped via a cap, which too can be clear for viewing effluent fluid. Drain container 50b also includes a drain fluid inlet, which in one embodiment is a drain fluid port 128 located on removable reservoir 120 of FIG. 15.

One difference between drain container 50b and drain container 50a is the provision of a transparent or clear effluent viewing window 166 located on the front surface 152 of container 50b. Effluent viewing window 166 allows the patient or caregiver to view the effluent fluid to see if it is cloudy or clear, cloudy indicating possible onset of peritonitis. It should be appreciated that viewing window 166 can be located in other suitable areas on container 50b.

Container 50b also includes an alternative sample reservoir 120, which is connected removably and sealably to front surface 152 of container 50b. Alternative reservoir 120 is shown in detail in FIG. 15. As seen in FIG. 15, alternative reservoir 120 includes a straight cylinder 122, which defines a single inlet hole 124. Here again, inlet hole 124 extends a suitable distance down into container 50b from front surface 152 when mounted into container 50b, as described above for drain container 100. A tube stop end 126 is sealed permanently or removably (e.g., via threads) to cylindrical housing 122. Tube stop end 126 is sized to fit sealingly into an opening on front surface 152 of container 50b. Cap 126 includes a drain tube port 128, which is sized to allow drain tube 18 to fit sealingly through the port.

Figure 16:
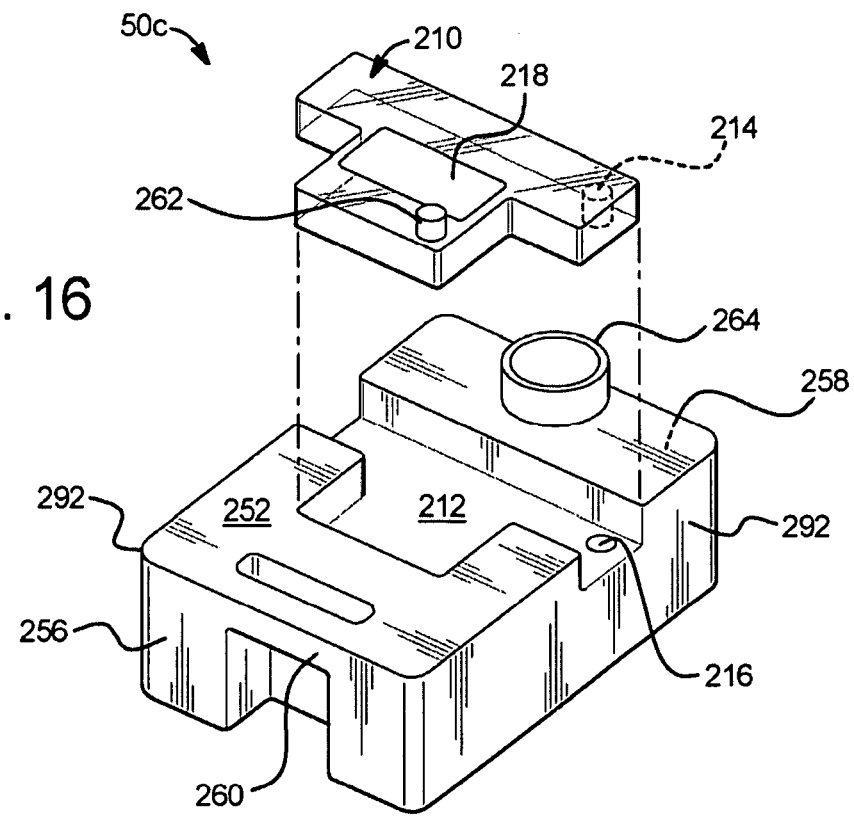
FIG. 16 is a perspective view of a further embodiment of a drain container of the present disclosure having a further alternative fluid reservoir.

Referring now to FIG. 16, drain container 50c illustrates another alternative drain container of the present disclosure. Container 50c includes many of the same features as containers 50a and 50b, such as a front surface 252, a rear surface (not seen in FIG. 16), a top surface 256 defining a handle 260 at front surface 252, a bottom surface 258 and sidewalls 292. Drain container 50c also includes a drain fluid inlet 262 and a drain fluid outlet 264.

The primary difference between drain container 50c and the other containers is that drain container 50c includes a larger removable reservoir 210, which in the illustrated embodiment has generally a T-shape. In the illustrated embodiment, reservoir 210 is mounted into a mating channel 212 defined in front surface 252 and in a small portion of side surfaces 292. Reservoir 210 includes drain fluid inlet 262, such that drained fluid from drain tube 18 initially enters reservoir 210 and flow from the reservoir via port 214 drain container 50c through a sealingly mating hole or aperture 216 formed in channel 212 of front surface 252 of container 50c. Reservoir 210 also includes a viewing window 218 (Alternatively all or some of the surface of reservoir 210 is formed of a clear or transparent material). Viewing window 218 allows the patient or caregiver to view effluent fluid immediately as it enters reservoir 210 during treatment and also allows the patient or caregiver to view the condition of the effluent that has mixed over the course of treatment, which eventually fills up within drain container 50c to the point that effluent fluid flows upward through port 214 into reservoir 210. Reservoir 210 in the operable orientation shown in collects a sample that is a mixture of each of the drains of the patient's therapy. In one embodiment, reservoir 210 is removed at the end of therapy for cleaning.

It should appreciated that concepts described in connection with reservoir 210 and drain container 50c are not limited to the particular shape of reservoir 210 shown in FIG. 16. In a further alternative implementation, inlet 262 is provided elsewhere on front surface 252 or other surface of drain container 50c.

Referring now to FIG. 17, wheel assembly 200 discussed above in connection with container 50b of FIG. 14 is illustrated in more detail. As described above, assembly 200 includes a pair of wheels 204 attached rotatably to an axle 202, which is in turn coupled to sides members or shafts 206. In FIG. 17, shafts 206 are larger diameter shafts that accept legs of a U-shaped telescoping handle 208. The legs have a smaller diameter that fits moveably within shafts 206. Handle 208 can have a button that is pressed to allow the legs of the handle to snap-fit into a retracted or extended position as desired. Handle 208 makes moving any of drain containers 50 (referring collectively to containers 50a to 50c) easier because the patient or caregiver can walk more upright during such movement. Telescoping handle 208 can replace or be provided in addition to the handles located integrally on drain containers 50. The drain container handles help to load and unload the drain containers from wheel assembly 200 and to maneuver the drain container once removed.

Figure 18:
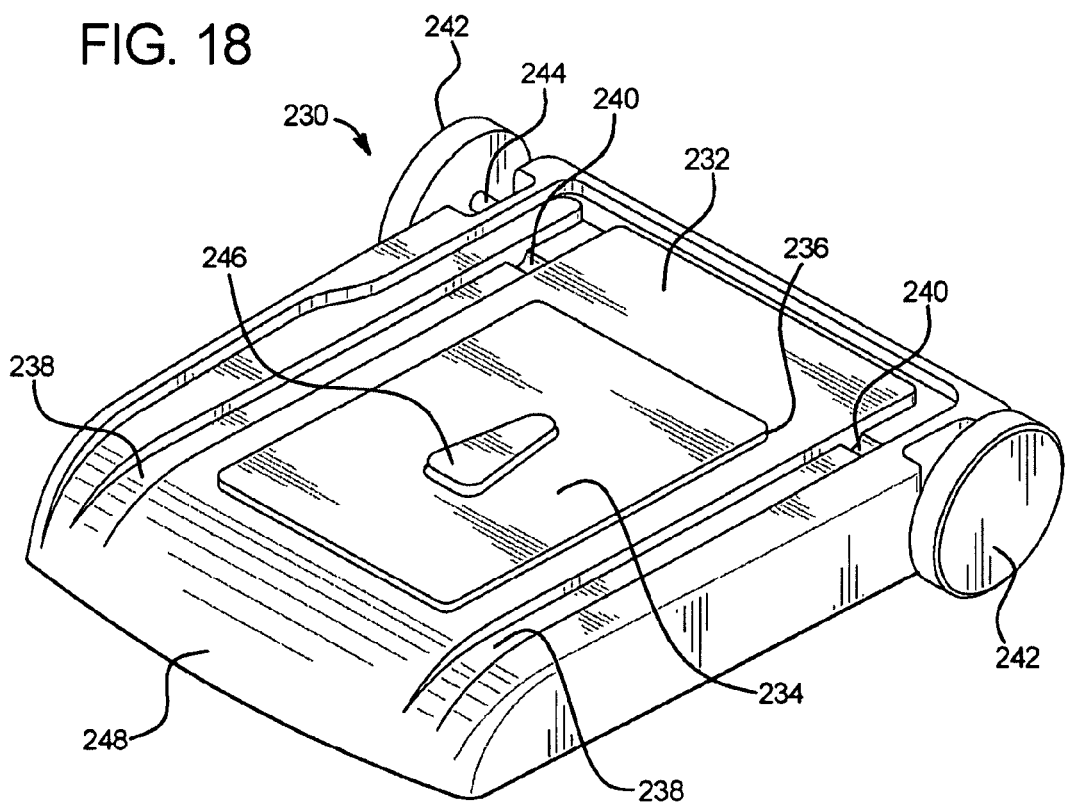
FIG. 18 is a perspective view of one embodiment of a load cell useable with any of the drain containers discussed herein.

Referring now to FIG. 18, load cell assembly 230 illustrates one suitable load cell for use with any of the drain containers 50 discussed herein. Assembly 230 includes a platform 232 that surrounds a load cell 234, which floats within a cutout 236 of platform 232. Platform 232 further includes or defines wheel tracks 238, which are sized in width to accept wheels 204 of wheel assembly 200. Tracks 238 each include an indent or stop 240, which is configured to grab and hold wheels 204 of assembly 200 for and during therapy and in turn hold drain container 50, which is coupled to assembly 200.

FIG. 1 illustrates one embodiment in which load cell 12 is placed above wheeled base 28. Load cell assembly 230 of FIG. 18 illustrates an alternative embodiment in which assembly 230 itself rests on the ground. Assembly 230 accordingly includes wheels 242, which connect to an axle 244, which in turn is coupled rotatably to platform 232 of load cell assembly 230. In this manner, the patient can roll assembly 230 with or without drain container 50 when the patient needs to move the entire medical fluid treatment system 10.

When the patient wishes to remove drain container 50 from load cell assembly 230, the patient rotates wheel assembly 200 and likewise rotates drain container 50 off of assembly 230, so that the female keying feature (e.g., feature 68 of container 50a) of drain container 50 is lifted off of a mating male keying feature 246 formed in the plate of load cell 232. The patient or caregiver then pulls wheels 204 of assembly 200 out of indents 240 of track 238 and rolls drain container 50 and associated wheel assembly 200 down tracks 238, off of a tapered front edge 248 of platform 232 and to the desired drain area of the patient's house, clinic or center as the case may be.

In the illustrated embodiment, the load cell keying feature 246 is raised from load cell 234 to mate with a female or recessed mating keying feature (e.g., feature 68 of container 50a) of the drain container. Alternatively, the keying feature on load cell 234 is indented or female in nature, while the mating keying feature of drain container is a projected or male type keying feature.

Platform 232 of load cell assembly 230 is made of relatively rugged and durable material, such as a polycarbonate, acrylonitrile butadiene styrene ("ABS") or a combination thereof. Load cell 234 in one embodiment includes a metal plate, attached to strain gauge apparatus, which is known in the art. Load cell 234 mates with projected surface 69 (see FIGS. 2, 4 and 5) of container 50a (or other like surface of other containers herein). Projected surface 69 allows load cell 234 to measure the full weight of container 50a. Electronics of instrument 20 are programmed to know the dry weight of container 50 to determine the absolute weight of effluent and/or to substrate the weight of container 50 at the beginning of treatment from the weight of container and effluent at the end of treatment to determine the total weight of effluent collected.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A dialysis system comprising:
a source of dialysis fluid;
at least one pump for pumping dialysate to or from a patient or dialyzer; and
a drain container configured to receive effluent dialysis fluid from the patient or dialyzer through a drain tube, the drain container including an at least semi-rigid body, the body including a handle, a drain tube receiving portion, a removable reservoir including a fluid holding portion and at least one aperture formed on the wall of the removable reservoir above the fluid holding portion in order to allow fluid to flow into the reservoir from the drain container, a separate effluent outlet on a same surface of the container as the drain tube receiving portion, a spout, and wherein at least a portion of the body is non-opaque such that effluent dialysis fluid inside the at least semi-rigid body can be viewed.

2. The dialysis system of claim 1, wherein the drain container includes a cap that threads over the spout, the cap forming at least part of the non-opaque portion of the body.

3. The dialysis system of claim 1, wherein the drain container includes a cap that connects to the drain tube receiving portion, the cap forming at least part of the non-opaque portion of the body.

4. The dialysis system of claim 1, wherein at least a portion of the removable reservoir is configured to extend into the drain container.

5. The dialysis system of claim 4, wherein at least a portion of the reservoir is non-opaque, forming at least part of the non-opaque portion of the body.

6. The dialysis system of claim 1, wherein the body is made from multiple pieces, at least one of the pieces being at least partially non-opaque and forming at least part of the non-opaque portion of the body.

7. The dialysis system of claim 1, the body including a non-opaque window, the window forming at least part of the non-opaque portion of the body.

8. The dialysis system of claim 1, the body of the drain container including at least one indented feature configured to allow the drain container to be rested along an edge of a toilet or bathtub to remove effluent dialysis fluid from the drain container.

9. The dialysis system of claim 1, which includes a load cell, the load cell including a key feature formed on a plate of the load cell, the drain container including a mating feature sized to mate with the key feature when the drain container is placed into the load cell.

10. The dialysis system of claim 1, which includes a plurality of wheels attached to the body of the drain container.

11. The dialysis system of claim 10, the wheels attached to a wheel assembly, the drain container attached removably to the wheel assembly.

12. A dialysis system comprising:
a source of dialysis fluid;
at least one pump for pumping dialysate to or from a patient or dialyzer; and
a drain container configured to receive effluent dialysis fluid from the patient or dialyzer through a drain tube, the drain container including an at least semi-rigid body, the body including a handle, a drain tube receiving portion, a removable reservoir including a fluid holding portion and at least one aperture formed on the wall of the removable reservoir above the fluid holding portion in order to allow fluid to flow into the reservoir from the drain container, a spout, an effluent outlet located on a same side of the container as the spout and the drain tube receiving portion, and at least one indented feature configured to allow the drain container to be rested along an edge of a toilet or bathtub to remove effluent dialysis fluid from the drain container, wherein at least a portion of the body is non-opaque such that effluent dialysis fluid inside the at least semi-rigid body can be viewed.

13. The dialysis system of claim 9, wherein the surface is a front surface of the body, and the mating feature is located on an opposing rear surface of the body.

14. The dialysis system of claim 1, wherein the spout is located on the same surface as the effluent outlet and the drain tube receiving portion.

* * * * *